United States Patent [19]
Schweden et al.

[11] Patent Number: 5,672,487
[45] Date of Patent: Sep. 30, 1997

[54] RECOMBINANT PRODUCTION OF PROTEINS IN YEAST

[75] Inventors: Jürgen Schweden, Neustadt; Claus Bollschweiler, Heidelberg; Michael Piontek, Essen; Ulrike Weydemann, Köln; Gerd Gellissen, Wülfrath, all of Germany

[73] Assignees: BASF Aktiengesellschaft, Ludwigshafen; Rhein Biotech Gesellschaft, Duesseldorf, both of Germany

[21] Appl. No.: 619,598

[22] Filed: Mar. 29, 1996

[30] Foreign Application Priority Data

Oct. 28, 1993 [DE] Germany .............. 43 36 810.7

[51] Int. Cl.$^6$ ..................................... C12P 21/02
[52] U.S. Cl. ........................ 435/69.1; 435/172.3
[58] Field of Search ................ 435/69.1, 172.3

[56] References Cited

PUBLICATIONS

Romanos et al., Yeast, vol. 8; 1992, pp. 423–488.
Two yeast acid phosphatase structural . . . , EMBO Jrnl. vol. 1 No. 6, pp. 675–680, 1982, Meyhack et al.
Nucleotide sequence of the yeast . . . , Nucleic Acids Res. vol. 11, No. 6, 1983, Taussig et al.
α–Factor–directed synthesis and secretion . . . , Proc. Natl. Acid. Sci., vol. 81, pp. 4642–4646, Aug. 1984, Brake et al.

*Primary Examiner*—James Ketter
*Attorney, Agent, or Firm*—Keil & Weinkauf

[57] ABSTRACT

A process for the recombinant production of proteins in yeast comprises transforming the yeast with an expression cassette which comprises the following structural elements encoded:

L-A-P-GEN where

L is a leader sequence of an animal peptide neurohormone,
A is an adaptor producing an alpha-helix structure,
P is a processing signal and
GEN is a structural gene for the required protein.

3 Claims, No Drawings

RECOMBINANT PRODUCTION OF PROTEINS IN YEAST

The present invention relates to a process for the recombinant production of proteins in yeasts.

The recombinant production of proteins in yeasts is known.

Proteins can be expressed by heterologous genes intracellularly or secreted directly into the medium. The precondition for the latter is that a signal sequence is fused in front of the heterologous protein or gene. In S. cerevisiae, the signal sequences of the genuine secretory proteins for the α factor pheromone (Brake A. J., et al., Natl. Acad. Sci. USA 81 (1984) 4642–4616), invertase (Taussig R. & Carlson M., Nucleic Acids Res. 11 (1983) 1943–1954) and acid phosphatase (Meyhack B. et al., EMBO J. 1 (1982) 675–680) have been used for the secretion of heterologous proteins (Kingsman S., et al., In: Russel G. E. (Ed.) Yeast Biotechnology (pp. 113–152). Intercept Ltd., Wimborne, Dorset (1988); Chiron EP 116 201).

Fusions with this pre-pro fragment also lead in other yeasts to the secretion of heterologous proteins, so that it can be assumed that the processing and secretion mechanism are similar (Gellissen G. et al., Biotech. Adv. 10 (1992) 179–189); Vedvick T. et al., J. Ind. Microbiol. 7 (1992) 197–202).

The genuine signal sequences of a heterologous protein are also recognized in yeasts.

In the yeast Hansenula polymorpha, the glucoamylase leader sequence (GAM1) from Schwanniomyces occidentalis is recognized as signal sequence, and it is possible to secrete correctly processed glucoamylase (G. Gellissen et al., Biotechnology 9 (1991) 291–295). However, this signal sequence does not lead to the secretion of gene products foreign to yeasts, for example it is not possible to secrete the protein hirudin therewith.

It is an object of the present invention to provide a process for the recombinant production of proteins, in particular of proteins which are foreign to yeasts, ie. heterologous, in the yeast Hansenula, which ensures efficient secretion and correct processing for a large number of proteins.

We have found that this object is achieved by a process for the recombinant production of proteins in yeast, which comprises transforming the yeast with an expression cassette which comprises the following structural elements encoded:

L-A-P-GEN where
L is a leader sequence of an animal peptide neurohormone,
A is an adaptor producing an alpha-helix structure,
P is a processing signal and
GEN is a structural gene for the required protein.

Suitable leader sequences are all leader sequences from animal peptide neurohormones. Particularly suitable leader sequences are those derived from neurohormones from invertebrates such as insects and molluscs.

Examples of such animal peptide neurohormones are PBAN from the corn earwig (Davis et al., Proc. Natl. Acad. Sci. USA 89 (1992) 142–146), the 5-KD-peptide from grasshoppers (Eur. J. Biochem. 187 (1990) 249–254), hyperglycemic hormone from the shore crab (FEBS Letter, 257 (1989) 31–34), and vasotocin from the toad (Proc. Natl, Acad. Sci. USA 84 (1987) 3043–3046).

Particularly suitable for the process according to the invention is the leader sequence from the hyperglycemic hormone of the shore crab. It consists of amino acids Nos. 1 to 26 in sequence SEQ ID NO:1.

Suitable sequences as adaptor A are all those which code for a polypeptide which contains an alpha-helix structure. The presence of an alpha-helix structure can be determined by the algorithm of Garnier et al. (J. Mol. Biol. 120 (1978) 97–120). It is particularly easy to determine, using commercially obtainable computer programs based on this algorithm, whether a polypeptide sequence ought to have an alpha-helix structure.

As a rule, sequences which are very suitable as adaptor are all those for which the computer program Microgenie® (Beckmann) calculates for ALPHA a larger positive value than for the three other possible structures (BETA, TURN, COIL) for a peptide sequence of at least four amino acids in the region of the processing site A-P-GEN.

The length of the adaptor sequence A can vary within wide limits for the use according to the invention. As a rule, it is from five to one hundred amino acids.

The sequence which is 38 amino acids long, SEQ ID NO:1 Nos. 27–64, is preferably used as adaptor sequence A.

This sequence can be used as adaptor sequence directly or, particularly preferably, after extension at the C terminus by one to four amino acids. Parts of this sequence, preferably those obtained by N-terminal truncation, are also very suitable for the process according to the invention.

It is also possible, for example, by means of the computer program described above, for the parts which particularly contribute to the alpha-helix formation to be identified and also optimized in respect of the alpha-helix structure by exchange of individual amino acids.

The processing signal P serves to cleave the propeptide to the mature form. Normally, a sequence of basic amino acids, preferably of Lys or Arg, is used as processing signal. A very suitable processing signal is the KEX2 recognition site from S. cerevisiae, which consists of the dipeptide Lys-Arg and is also recognized by other yeasts. This dipeptide can also be used in duplicated form as processing signal. The sequence Lys-Arg is preferred as P.

Heterologous and homologous genes can be used as structural gene GEN for the protein to be produced. The genes can be isolated from the appropriate organisms or prepared by synthesis. In the case of chemical gene synthesis it is also possible, if required, to adapt the codon usage to the producer organism.

Eukaryotic genes and viral genes are preferably employed as structural genes. The process according to the invention succeeds particularly well for the production of thrombin inhibitors, for example hirudin. This process is also very suitable for the production of human polypeptides, for example peptide hormones, growth factors and lymphokines.

The abovementioned structural elements are arranged in a known manner in the sequence L-A-P-GEN in an expression cassette. The linkage normally takes place by ligation of compatible restriction fragments or by chemical synthesis.

The expression cassettes may furthermore contain a number of conventional regulation signals such as promoters, ribosome binding sites and terminators, which are functionally connected to the structural elements L-A-P-GEN according to the invention.

The expression cassette can be part of an autonomously replicating or else an integrative vector. The construction of an expression vector using the expression cassette is described in Example 1.

The yeast is transformed with the appropriate expression vector. This can take place, for example, by the protocol described in Example 2.

Stably expressing clones which are suitable as producer organism in the process according to the invention are isolated from the yeast transformed in this way. The producer organisms are cultivated under conventional conditions and produce the required protein in a constitutive or inducible manner depending on the regulation elements selected. The protein is secreted by the producer organism into the surrounding medium, from where it can easily be isolated and purified.

Purification from the medium takes place as a rule, after the producer organism has been removed, by purification processes familiar in protein chemistry.

The process according to the invention provides correctly processed mature proteins without the faulty processing otherwise observed. This process therefore leads to a high yield of mature protein and considerably facilitates the subsequent purification steps. This process can therefore be employed particularly well for the production of drugs based on pharmaceutical proteins.

The following examples explain the invention further.

EXAMPLE 1

Construction of Vectors for the Secretory Expression of Recombinant Proteins from the Yeast Strain *Hansenula polymorpha*

This example describes the construction of expression vectors which are used in the production according to the invention of recombinant proteins in *Hansenula polymorpha*. The expression cassette used for this purpose comprises inter alia the following constituents:
Leader: Amino acid 1–26 of SEQ ID NO: 1
Adaptor: Amino acid 27–64 of SEQ ID NO: 1
P: Amtino acid 65–66 of SEQ ID NO: 1
GEN: Hirudin gene (SEQ ID NO: 2)

The construct was assembled from two DNA fragments. The first fragment comprised the leader-adaptor-processing sequences indicated above and the 5'-terminal nucleotides of the hirudin gene for amino acid 1 (Val) to 7 (Thr) SEQ ID NO: 2 (L-A-P-5'-Hir fragment). The second fragment was derived from the remaining amino acids of the hirudin gene (8 (Glu) to 65 (Gln), SEQ ID NO: 2) (3'-Hir fragment).

Two oligonucleotides SEQ ID NO: 3 and SEQ ID NO: 4 were synthesized to prepare the L-A-P-5'-Hir fragment. The two oligonucleotides have overlapping complementarity in the region of 20 nucleotides at their 3' ends.

In a PCR, the DNA molecules in the non-complementary single-stranded sections were filled in to give the double strand by addition of nucleoside triphosphates and polymerase. The DNA was amplified by addition of two amplification primers (SEQ ID NO: 5 and SEQ ID NO: 6) and PCR amplification. The resulting L-A-P-5'-Hir fragment was then cut at the 5' end with Eco RI and at the 3' end with Hinf I.

The 3'-Hir fragment was prepared starting from the known hirudin gene using two synthetic amplification primers (SEQ ID NO: 7 and SEQ ID NO: 8) and PCR amplification.

The fragment obtained in this way was then cut at the 5' end with Hinf I and the 3' end with Sal I.

Ligation of the 3'-end Hinf I site of the L-A-P-5'-Hir fragment to the 5'-end Hinf I site of the 3'-Hir fragment, and ligation of this DNA via Eco RI/Sal I into the vector pUC 18, completed the construct.

The L-A-P-Hir fragment was in turn isolated from this construct as EcoRI/Bgl II fragment and ligated into the appropriately prepared H. polymorpha expression vector pFMD 13025 (Gellissen G. et al., TIBTECH, 10 (1992) 413–417). This entails fusion of the 5' end of L-A-P-Hir to the H. polymorpha promoter and of the 3' end of the fragment to the H. polymorpha terminator. The expression cassette is now complete and a constituent of a shuttle vector with which both E. coli, for the purpose of propagation, and the yeast H. polymorpha, for the purpose of expression of the foreign gene, can be transformed.

The same L-A-P construction was fused to the gene for the thrombin inhibitor rhodniin from *Rhodnius prolixus* (WO 93/8282) and to the gene for the thrombin inhibitor moubatin from *Ornithodorus moubata* (WO 93/9232). The expression cassettes obtained in this way were employed in a similar way to the hirudin gene fusions for constructing *Hansenula polymorpha* expression vectors.

EXAMPLE 2

Transformation of *Hansenula polymorpha* with the Expression Vectors

The host strain for the transformation is an auxotrophic mutant obtained by EMS mutagenesis: a strain with a deficiency for orotidine-5'-phosphate dehydrogenase (ura$^-$). The reversion rate of this uracil mutant can be neglected.

Competent cells of this strain were obtained in the following way (method of Dohmen et al., Yeast 7 (1992) 691–692):

10 ml of yeast complete medium (YPD) were inoculated with the host strain and cultivated by shaking at 37° C. overnight. This preculture was transferred into 200 ml of YPD medium and cultivated by shaking at 37° C. until the $OD_{600\ nm}$=0.6–1.0.. The cells were washed with 0.5 ml volume of solution A (1M sorbitol, 10 mM bicine pH 8.35, 3% ethylene glycol) at room temperature and subsequently resuspended in 0.02 volume of solution A.

After adding 11 µl of DMSO, the aliquots were stored at –70° C. until the transformation was carried out.

For the transformation, 10 µg of plasmid DNA and 100 µl of cold 0.1M calcium chloride solution were added directly to the frozen competent cells.

After rapid thawing at 37° C., each transformation mixture was incubated with 1.0 ml of solution B (40% polyethylene glycol PEG 3350, 200 mM bicine pH 8.35) at 37° C. for one hour. The cells were then washed in 1 ml of solution C (150 mM NaCl, 10 mM bicine pH 8.35), resuspended in 200 µl of solution C and plated onto selective medium (YNB glucose, complementation of the uracil deficiency by ura$^+$ expression plasmids). Incubation took place at 37° C. for 3–5 days.

EXAMPLE 3

Isolation of Mitotically Stable Clones

The recombinant expression plasmids used for transforming H. polymorpha are autonomously replicating and can integrate spontaneously into the yeast genome. They form a multimeric structure therein: the plasmid monomers are connected together head to tail.

Several copies of the expression cassette therefore contribute to production of the recombinant gene product. The productivity of a recombinant strain is linearly related to the number of integrated expression cassettes over a wide range. Multimeric integration of the foreign DNA into the yeast genome and isolation of mitotically stable clones was achieved in the following way:

The transformants were inoculated from the agar plates with selective medium into 3 ml of appropriate liquid medium and passaged, ie. repeated transfer into fresh YNB glucose medium (50 µl in 3 ml of medium, cultivations at 37° C.) over a period of 1–2 weeks. During this passaging, the plasmid DNA integrated into the yeast genome so that mitotically stable clones were then obtained.

The mitotic stability was tested in the following way:

Three transfers were made from the last passaging culture in YNB glucose medium into complete medium (YPD) and cultivated at 37° C. for 1–2 days. The diluted culture was then plated onto complete medium and onto selective medium. Mitotically stable transformants give approximately the same number of colonies on the two media. It is thus possible to isolate mitotically stable subtransformants (Z. A. Janowicz et al., Yeast 7 (1991) 431–443).

EXAMPLE 4

Expression of Foreign Gene

For expression studies, the passaged transformants were inoculated into 3 ml of YNB medium containing 1% glycerol or 1% methanol in order to induce MOX or FMD promoters. The cells were cultivated at 37° C. for two days and then spun down, and the culture supernatant was tested for foreign protein (Western blot, ELISA, activity assay).

50 ml of synthetic medium containing 1.5% glycerol in a 500 ml Erlenmeyer flask with baffles were inoculated with efficiently secreting mitotically stable transformants and incubated to $OD_{600\ nm}=10$. HPLC analyses of corresponding culture supernatants showed that the hirudin variant is completely correctly processed on use of the sequence SEQ ID NO: 1 Nos. 1 to 64 as leader-adaptor.

EXAMPLE 5

Fermentation of Recombinant Yeast Strains

The recombinant yeast strains were fermented in synthetic media (double-concentrated YNB medium 2.8 g/l (Difco) containing 10 g/l ammonium sulfate) which had been either introduced completely at the start of the fermentation or were fed in during the fermentation.

The carbon sources employed were glycerol and methanol or mixtures of glycerol and methanol. The fermentation was started with glycerol as the sole carbon source ($\geq 1\%$ glycerol final concentration in the fermenter during the initial growth phase).

After sterilization of the medium, it was inoculated with 1 l of preculture so that the initial $OD_{600\ nm}$ was about 1.

The fermentation took place in two phases: an initial growth phase with a higher glycerol concentration (1%) was followed by a production phase with a lower glycerol concentration (<0.5%) or constant methanol concentration (1%) or a mixture of glycerol and methanol (0.1–0.4% glycerol and 0.2–1.0% methanol).

The carbon source was fed in where appropriate with various control possibilities (continuously or $pO_2$-coupled.)

During the fermentation there was addition of ammonium sulfate to a final concentration of 5 g/l, thiamine to a final concentration of 0.1 g/l and biotin to a final concentration of 0.3 mg/l.

The pH of the fermentation was kept constant at 4.0 by adding aqueous ammonia; the fermentation temperature was 37° C.

The recombinant yeast strains fermented in this way provided a gene product (hirudin) which was 100% correctly processed.

---

We claim:

1. A process for the recombinant production of proteins in yeast, which comprises transforming the yeast with an expression cassette which comprises the following structural elements encoded:

L-A-P-GEN where

L is a leader sequence of an animal peptide neurohormone,

A is an adaptor producing an alpha-helix structure,

P is a processing signal and

GEN is a structural gene for the required protein growing the transformed yeast in a suitable growth medium; and recovering said protein.

2. A process as claimed in claim 1, wherein

L is amino acid sequence 1–26 of SEQ ID NO: 1,

A is amino acid sequence 27–64 of SEQ ID NO: 1 and

P is amino acid sequence 65–66 of SEQ ID NO: 1.

3. A process as claimed in claim 1, wherein said yeast is of the genus Hansenula, Saccharomyces, Kluyveromyces or Pichia.

* * * * *

UNITED STATES PATENT AND TRADEMARK OFFICE
CERTIFICATE OF CORRECTION

PATENT NO. : 5,672,487
DATED : September 30, 1997
INVENTOR(S) : SCHWEDEN et al.

It is certified that error appears in the above-identified patent and that said Letters Patent is hereby corrected as shown below:

On the cover page, correct item [73], the assignee, to read as follows:

--[73] Assignees: BASF Aktiengesellschaft, Ludwigshafen; Rhein Biotech Gesellschaft für neue biotechnische Produkte mbH, Duesseldorf, both of Germany.--

Column 12, claim 1, line 1, after "protein" insert --;--.

Signed and Sealed this

Twenty-second Day of December, 1998

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 8

( 2 ) INFORMATION FOR SEQ ID NO: 1:

( i ) SEQUENCE CHARACTERISTICS:
        ( A ) LENGTH: 142 amino acids
        ( B ) TYPE: amino acid
        ( D ) TOPOLOGY: linear ( i i ) MOLECULE TYPE: peptide ( i i i ) HYPOTHETICAL: no ( i v ) ANTI-SENSE: no ( v ) FRAGMENT TYPE: N terminus ( v i ) ORIGINAL SOURCE:
        ( A ) ORGANISM: Carcinus maenas ( i x ) FEATURE:
        ( A ) NAME/KEY: peptide
        ( B ) LOCATION: 1..26
        ( D ) OTHER INFORMATION: /label =leader ( i x ) FEATURE:
        ( A ) NAME/KEY: peptide
        ( B ) LOCATION: 27..66
        ( D ) OTHER INFORMATION: /label =adaptor ( i x ) FEATURE:
        ( A ) NAME/KEY: peptide
        ( B ) LOCATION: 67..142

( D ) OTHER INFORMATION: /label =CHH ( x i ) SEQUENCE DESCRIPTION: SEQ ID NO: 1:

| Met | Tyr | Ser | Lys | Thr | Ile | Pro | Ala | Met | Leu | Ala | Ile | Ile | Thr | Val | Ala |
| 1 | | | | 5 | | | | | 10 | | | | | 15 | |

| Tyr | Leu | Cys | Ala | Leu | Pro | His | Ala | His | Ala | Arg | Ser | Thr | Gln | Gly | Tyr |
| | | | 20 | | | | | 25 | | | | | 30 | | |

| Gly | Arg | Met | Asp | Arg | Ile | Leu | Ala | Ala | Leu | Lys | Thr | Ser | Pro | Met | Glu |
| | | 35 | | | | | | 40 | | | | 45 | | | |

| Pro | Ser | Ala | Ala | Leu | Ala | Val | Glu | Asn | Gly | Thr | Thr | His | Pro | Leu | Glu |
| | 50 | | | | | 55 | | | | | 60 | | | | |

| Lys | Arg | Gln | Ile | Tyr | Asp | Thr | Ser | Cys | Lys | Gly | Val | Tyr | Asp | Arg | Ala |
| 65 | | | | | 70 | | | | 75 | | | | | | 80 |

| Leu | Phe | Asn | Asp | Leu | Glu | His | Val | Cys | Asp | Asp | Cys | Tyr | Asn | Leu | Tyr |
| | | | | 85 | | | | | 90 | | | | | 95 | |

| Arg | Thr | Ser | Tyr | Val | Ala | Ser | Ala | Cys | Arg | Ser | Asn | Cys | Tyr | Ser | Asn |
| | | | 100 | | | | | 105 | | | | | 110 | | |

| Leu | Val | Phe | Arg | Gln | Cys | Met | Asp | Asp | Leu | Leu | Met | Met | Asp | Glu | Phe |
| | | | 115 | | | | 120 | | | | | 125 | | | |

| Asp | Gln | Tyr | Ala | Arg | Lys | Val | Gln | Met | Val | Gly | Arg | Lys | Lys |
| | 130 | | | | | 135 | | | | | 140 | | |

( 2 ) INFORMATION FOR SEQ ID NO: 2:

( i ) SEQUENCE CHARACTERISTICS:
        ( A ) LENGTH: 65 amino acids
        ( B ) TYPE: amino acid
        ( D ) TOPOLOGY: linear ( i i ) MOLECULE TYPE: protein ( i i i ) HYPOTHETICAL: no ( i v ) ANTI-SENSE: no ( x i ) SEQUENCE DESCRIPTION: SEQ ID NO: 2:

| Val | Val | Tyr | Thr | Asp | Cys | Thr | Glu | Ser | Gly | Gln | Asn | Leu | Cys | Leu | Cys |
| 1 | | | | 5 | | | | | 10 | | | | | 15 | |

| Glu | Gly | Ser | Asn | Val | Cys | Gly | Gln | Gly | Asn | Lys | Cys | Ile | Leu | Gly | Ser |
| | | | 20 | | | | | 25 | | | | | 30 | | |

| Lys | Gly | Glu | Arg | Asn | Gln | Cys | Val | Thr | Gly | Glu | Gly | Thr | Pro | Arg | Pro |
| | | | 35 | | | | | 40 | | | | | 45 | | |

| Gln | Ser | His | Asn | Asp | Gly | Asp | Phe | Glu | Glu | Ile | Pro | Glu | Glu | Tyr | Leu |
| | 50 | | | | | 55 | | | | | 60 | | | | |

| Gln |
| 65 |

( 2 ) INFORMATION FOR SEQ ID NO: 3:

( i ) SEQUENCE CHARACTERISTICS:
        ( A ) LENGTH: 140 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 3:

```
GGGGGGGAAT  TCATGTATAG  CAAAACTATT  CCCGCCATGC  TAGCAATCAT  CACCGTAGCC    60
TACCTATGCG  CACTCCCGCA  CGCACACGCA  CGCTCCACGC  AAGGCTACGG  ACGCATGGAT   120
CGCATCCTGG  CGGCCTTGAA                                                  140
```

( 2 ) INFORMATION FOR SEQ ID NO: 4:

( i ) SEQUENCE CHARACTERISTICS:
        ( A ) LENGTH: 122 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 4:

```
GGGGGGGATT CAGTGCAGTC AGTGTAAACA ACCCTCTTTT CCAACGGGTG TGTAGTTCCA      60

TTCTCCACCG CTAGGGCTGC GCTGGGCTCC ATTGGCGAGG TTTTCAAGGC CGCCAGGATG     120

CG                                                                    122
```

( 2 ) INFORMATION FOR SEQ ID NO: 5:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 5:

```
GGGGGGGAAT TCATGTATAG C                                                21
```

( 2 ) INFORMATION FOR SEQ ID NO: 6:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 6:

```
GGGGGGGATT CAGTGCAGTC A                                                21
```

( 2 ) INFORMATION FOR SEQ ID NO: 7:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 7:

```
GGGGGGGAAT CCGGTCAGAA CCTGTGCCTG TGCGAA                                36
```

( 2 ) INFORMATION FOR SEQ ID NO: 8:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 8:

```
GGGGGGGTCG ACCCTAGATC TCTATTACTG CAGGTATTCT TCCGG                      45
```